(12) United States Patent
Nagaoka et al.

(10) Patent No.: US 11,020,063 B2
(45) Date of Patent: Jun. 1, 2021

(54) SUPPORT SYSTEM

(71) Applicant: Paramount Bed Co., Ltd., Tokyo (JP)

(72) Inventors: Hiroshi Nagaoka, Tokyo (JP); Takeshi Nagayasu, Tokyo (JP); Hironobu Maezawa, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 59 days.

(21) Appl. No.: 16/424,997

(22) Filed: May 29, 2019

(65) Prior Publication Data

US 2019/0380663 A1 Dec. 19, 2019

(30) Foreign Application Priority Data

Jun. 15, 2018 (JP) .............................. JP2018-114384

(51) Int. Cl.
| | |
|---|---|
| *A61B 5/00* | (2006.01) |
| *A61B 5/0205* | (2006.01) |
| *A61B 5/024* | (2006.01) |
| *A61B 5/08* | (2006.01) |
| *A61B 5/16* | (2006.01) |

(Continued)

(52) U.S. Cl.
CPC ............ *A61B 5/747* (2013.01); *A61B 5/0205* (2013.01); *A61B 5/165* (2013.01); *A61B 5/4809* (2013.01);
(Continued)

(58) Field of Classification Search
CPC .......... A61M 2021/0083; A61M 21/00; G16H 80/00; G16H 40/67; G16H 40/63; G16H 40/20; A61B 5/165; A61B 5/4806; A61B 5/002; A61B 5/0205; A61B 5/024; A61B 5/08; A61B 5/4809; A61B 5/4857; A61B 5/747; A61B 2505/09; H04M 11/027; H04M 11/04; A61G 12/00; G08B 21/0415; G08B 21/0453; G08B 21/0461; H04L 67/12
(Continued)

(56) References Cited

U.S. PATENT DOCUMENTS

| | | | |
|---|---|---|---|
| 9,517,034 B2 | 12/2016 | Collins, Jr. et al. | |
| 2008/0172789 A1* | 7/2008 | Elliot | A61G 7/0528 5/616 |

(Continued)

FOREIGN PATENT DOCUMENTS

JP 2004-159804 A 6/2004

OTHER PUBLICATIONS

S. Uchida et al. "Sleep evaluation by a newly developed PVDF sensor non-contact sheet: a comparison with standard polysomnography and wrist actigraphy" Sleep and Biological Rhythms, 2011; pp. 178-187.

(Continued)

*Primary Examiner* — Carl H Layno
*Assistant Examiner* — Anh-Khoa N Dinh
(74) *Attorney, Agent, or Firm* — Harness, Dickey & Pierce, P.L.C.

(57) ABSTRACT

According to one embodiment, a support system includes a server and a terminal device capable of communicating with the server. The terminal device includes an input circuit configured to receive a first signal which indicates that a user is awake, and a controller coupled to the input circuit and configured to determine to provide support to the user based on the first signal.

19 Claims, 8 Drawing Sheets

(51) Int. Cl.

| | |
|---|---|
| *A61G 12/00* | (2006.01) |
| *A61M 21/00* | (2006.01) |
| *G08B 21/04* | (2006.01) |
| *G16H 40/20* | (2018.01) |
| *G16H 40/63* | (2018.01) |
| *G16H 40/67* | (2018.01) |
| *G16H 80/00* | (2018.01) |
| *H04L 29/08* | (2006.01) |
| *H04M 11/02* | (2006.01) |
| *H04M 11/04* | (2006.01) |

(52) U.S. Cl.
CPC ............ *A61B 5/4857* (2013.01); *A61G 12/00* (2013.01); *A61M 21/00* (2013.01); *G08B 21/0415* (2013.01); *G08B 21/0461* (2013.01); *G16H 40/67* (2018.01); *H04L 67/12* (2013.01); *H04M 11/027* (2013.01); *A61B 5/024* (2013.01); *A61B 5/08* (2013.01); *A61B 2505/09* (2013.01); *A61M 2021/0083* (2013.01)

(58) Field of Classification Search
USPC ............................................................ 705/2
See application file for complete search history.

(56) References Cited

U.S. PATENT DOCUMENTS

| | | | | |
|---|---|---|---|---|
| 2010/0042022 | A1* | 2/2010 | Kim | .................. A63B 22/0023 601/24 |
| 2013/0346108 | A1* | 12/2013 | Kamen | .................. G16H 40/63 705/3 |
| 2014/0180711 | A1* | 6/2014 | Kamen | .................. G16H 20/10 705/2 |
| 2015/0294549 | A1* | 10/2015 | Ribble | .................. G06Q 50/22 340/573.5 |
| 2015/0302539 | A1* | 10/2015 | Mazar | .................. G16H 40/20 705/3 |
| 2016/0022218 | A1* | 1/2016 | Hayes | .................. A61B 5/4809 600/301 |

OTHER PUBLICATIONS

T. Kogure et al. "Automatic Sleep/Wake Scoring from Body Motion in Bed: Validation of a Newly Developed Sensor Placed under a Mattress" Journal of Physiological Anthropology, 2011, pp. 103-109.

* cited by examiner

| FIRST PRIORITY \ SECOND PRIORITY | BEING ASLEEP | BEING AWAKE | NURSE'S INSTRUCTION | AMBIENT SOUND: LARGE AMBIENT LIGHT: BRIGHT | AMBIENT SOUND: SMALL AMBIENT LIGHT: DARK | HISTORY OF TREATMENT | CHANGE IN VITAL CONDITIONS |
|---|---|---|---|---|---|---|---|
| BEING ASLEEP | | | | | | | |
| BEING AWAKE | | | | | | | |
| NURSE'S INSTRUCTION | CONDITIONAL TALKING TO THE USER | TALKING TO THE USER | | | | | |
| AMBIENT SOUND: LARGE AMBIENT LIGHT: BRIGHT | CONDITIONAL TALKING TO THE USER | TALKING TO THE USER | TALKING TO THE USER | | | | |
| AMBIENT SOUND: SMALL AMBIENT LIGHT: DARK | NOT TALKING TO THE USER | CONDITIONAL TALKING TO THE USER | CONDITIONAL TALKING TO THE USER | | | | |
| HISTORY OF TREATMENT | CONDITIONAL TALKING TO THE USER | TALKING TO THE USER | TALKING TO THE USER | TALKING TO THE USER | CONDITIONAL TALKING TO THE USER | | |
| CHANGE IN VITAL CONDITIONS | TALKING TO THE USER | TALKING TO THE USER | TALKING TO THE USER | TALKING TO THE USER | TALKING TO THE USER | TALKING TO THE USER | |

F I G. 6

SUPPORT SYSTEM

CROSS-REFERENCE TO RELATED APPLICATIONS

This application is based upon and claims the benefit of priority from Japanese Patent Application No. 2018-114384, filed Jun. 15, 2018, the entire contents of which are incorporated herein by reference.

FIELD

Embodiments described herein relate generally to a support system.

BACKGROUND

In hospitals and nursing facilities, if there is a call request (hereinafter, "a nurse call") from a patient or a person who needs nursing care (hereinafter, "a care receiver"), a nurse or a care assistant, etc. needs to immediately visit the patient or the care receiver to respond to their needs.

BRIEF DESCRIPTION OF THE DRAWINGS

FIG. 6 is a table showing combinations of patient statuses, and circumstances for determining whether to talk to the patient, in the support system of a fourth embodiment;

DETAILED DESCRIPTION

Figure 1:
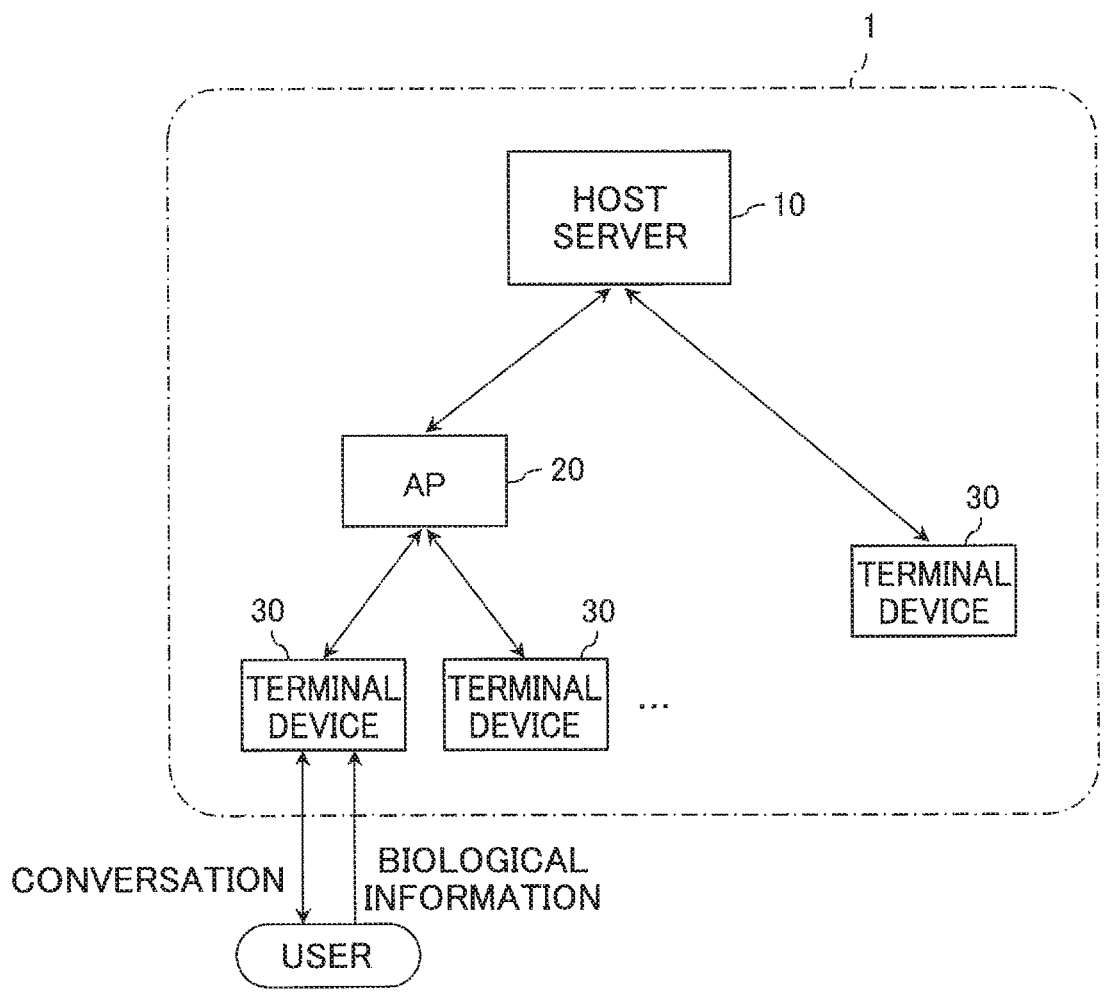
FIG. 1 is a diagram showing an overall configuration of a support system according to a first embodiment.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component," "system" and the like are intended to refer to, or comprise, a computer-related entity or an entity related to an operational apparatus with one or more specific functionalities, wherein the entity can be either hardware, or a combination of hardware and software in execution.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software stored on a non-transitory electronic memory or firmware that confers at least in part the functionality of the electronic components. While various components have been illustrated as separate components, it will be appreciated that multiple components can be implemented as a single component, or a single component can be implemented as multiple components, without departing from example embodiments. Further, the various embodiments can be implemented as a method, apparatus or article of manufacture using standard programming and engineering techniques to produce software, firmware, hardware or any combination thereof to control a computer to implement the disclosed subject matter. The term "article of manufacture" as used herein is intended to encompass a computer-readable (or machine-readable) device or computer-readable (or machine-readable) storage/communications media having computer program stored thereon. For example, computer readable storage media can comprise, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Embodiments described herein can be exploited in substantially any wireless communication technology, comprising, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet ac (HSPA), Z-Wave, Zigbee and other 802.XX wireless technologies and/or legacy telecommunication technologies.

In general, according to one embodiment, a support system includes a server and a terminal device capable of communicating with the server. The terminal device includes an input circuit configured to receive a first signal which indicates that a user is awake, and a controller coupled to the input circuit and configured to determine to provide support to the user based on the first signal.

1. First Embodiment

A support system of the first embodiment will be described. Hereinafter, a case where a support system 1 is used in a hospital, and one terminal device 30 of the support system 1 is given to each hospitalized patient, will be described as an example. A single terminal device 30 of the support system 1 may be provided to multiple patients (users), for example a group of patients who are accommodated in the same hospital room.

1.1 Overall Configuration of Support System

An overall configuration of the support system 1 will be described with reference to FIG. 1.

As shown in FIG. 1, the support system 1 includes a host server 10, a relay device (AP) 20, and a plurality of terminal devices 30.

The host server 10 controls the entire support system 1. The host server 10 controls to transmit and receive information to and from each terminal device 30. The host server 10 manages a status of each terminal device 30. The host server 10 controls to communicate with other devices through a network, etc. For example, the host server 10 communicates with a nurse call management system, a cloud computer, an external database, a medical system at a hospital, or a medical information terminal device, and the like, through a network.

The relay device 20 is additionally provided if, for example, a plurality of terminal devices 30 are used in a facility such as a hospital and the host server 10 can't directly communicate with the plurality of terminal devices 30. The relay device 20 functions as a relay station or spot when the host server 10 communicates with the plurality of terminal devices 30. The relay device 20 also functions as an access point for communications between the plurality of terminal devices 30. If, for example, a patient who receives care at home (hereinafter, "a home-care patient") uses the terminal device 30, the terminal device 30 may communicate with the host server 10 through a telephone line or network line, without involving the relay device 20.

The terminal device 30 checks or analyzes a user's condition and request, etc., and provides support to said user, based on biological information obtained from the user or conversation information obtained from conversations with the user.

1.2 Configuration of Terminal Device

Next, a configuration of the terminal device 30 will be described with reference to FIG. 2.

Figure 2:
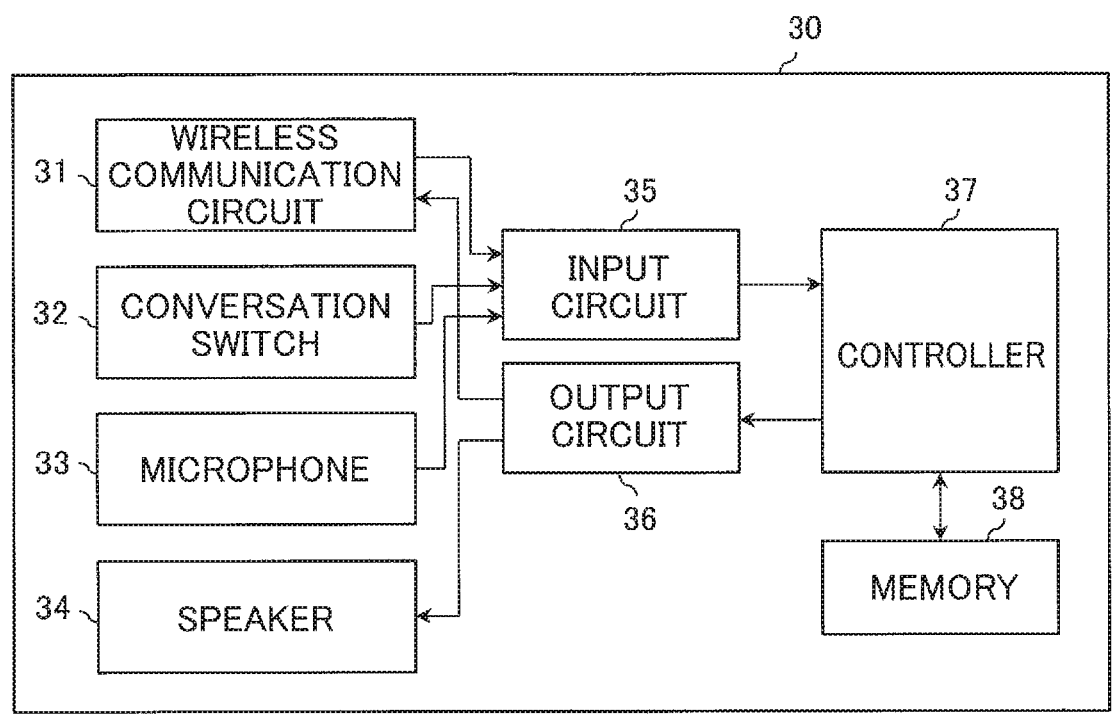
FIG. 2 is a diagram showing a configuration of a terminal device according to the first embodiment.

As shown in FIG. 2, the terminal device 30 includes a wireless communication circuit 31, a conversation switch 32, a microphone 33, a speaker 34, an input circuit 35, an output circuit 36, a controller 37, and a memory 38. The terminal device 30 may be installed on a robot, etc. which has a conversation function.

The wireless communication circuit 31 is coupled to the input circuit 35 and the output circuit 36, and is used for wireless communications with the host server 10, the relay device 20, or an external device. For example, the wireless communication circuit 31 transmits and receives signals to and from any of the following devices, either directly or via the host server 10 and the relay device 20: a nurse call (NC) management system, a device for monitoring patient's biological information, an automatic carrier device that carries items to a patient's room or bed (e.g., a bottle of water, a wheelchair, a cart, an IV pole, etc.), peripheral equipment (e.g., lighting, curtains, TV, etc. installed in the patient's room), an external database, a cloud computer, a medical information terminal device, medical equipment, or another terminal device 30 (e.g., a terminal device 30 used by another patient who is also in the same patient's room).

The wireless communication circuit 31 is used for communications between the terminal device 33 and the host server 10 via a telephone line or a network, when, for example, a home-care patient uses the terminal device 30. As an example of the device for monitoring biological information, "Nemuri SCAN" to detect the body motion or vibration for monitoring whether the patient is sleeping or awake, whether a posture of the patient is sitting-up (bodily activity), respiration, heart rate, and the like, of a patient who is on the bed, is known. The detail method to detect body vibration is disclosed in Japanese patent application No. 2002-327524 (a title of this application: an input-output detector whether the patient is in-bed or not, filing date: Nov. 11, 2011) and in Journal of Japanese Society of Sleep Research whose title is "Sleep evaluation by a newly developed PVDF sensor non-contact sheet: a comparison with standard polysomnography and wrist actigraphy" written by Sunao UCHIDA, Takuro ENDO, Kazue SUENAGA, Hideto IWAMI, Shinsuke INOUE, Eiji FUJIOKA, Ayako IMAMURA, Takafumi ATSUMI, Yoshitaka INAGAKI and Atsushi KAMEI, published in 2011. The entire contents of these patent applications are incorporated by reference. The detail method to determine the sleep state is disclosed in Journal of Physiological Anthropology whose title is "Automatic Sleep/Wake Scoring from Body Motion in Bed: Validation of a Newly Developed Sensor Placed under a Mattress" written by Takamasa Kogure, Shuichiro Shirakawa, Masato Shimokawa and Yuji Hosokawa, published in 2011. The entire contents of these patent applications are incorporated by reference.

In the following, a case where the wireless communication circuit 31 receives signals which indicates patient is awake (hereinafter, "waking signals"), signals which indicate a posture of patient is sitting-up in bed (hereinafter, "rise signals"), signals indicative of patient's respiration (hereinafter, "respiration signals"), and signals indicative of patient's heart rate (hereinafter, "heart rate signals") from Nemuri SCAN, will be described in the present embodiment. The wireless communication circuit 31 can receive signals relating to biological information from not only Nemuri SCAN but also other sensor devices, such as a wearable terminal device directly or indirectly attached to a patient.

The conversation switch 32 is coupled to the input circuit 35. The conversation switch 32 is operated by a user of the terminal device 30 (for example, a patient or a nurse) when the user wants to start or finish conversation with the terminal device 30. The conversation switch 32 may be omitted, and the starting or ending of a conversation may be conducted by a user's voice operation instead. There is a case where the terminal device 30 automatically starts or finishes a conversation in accordance with other input information, regardless of an operation of the conversation switch 32.

The microphone 33 is coupled to the input circuit 35 and used to have a conversation with a user.

The speaker 34 is coupled to the output circuit 36, and is used to have a conversation with a user or to notify a user of necessary information by sound.

The input circuit 35 is coupled to the controller 37. The input circuit 35 performs interface processing of signals with the wireless communication circuit 31, the conversation switch 32, and the microphone 33, etc., and with the controller 37.

The output circuit 36 is coupled to the controller 37. The output circuit 36 performs interface processing of signals with the wireless communication circuit 31 and the speaker 34, etc., and with the controller 37.

The memory 38 is coupled to the controller 37. The memory 38 stores, for example, various kinds of input information (for example, patient's personal information, biological information, and conversation information), conversation sentences (or phrases) which are used when the terminal devices 30 communicate with a patient, or a program executed when the devices provide support to a patient. As for the conversation sentences, different conversation sentences may be registered for respective patients, in addition to common phrases (such as "Good morning" and "Good night").

The controller 37 is composed of a central processing unit (CPU), and controls the entire terminal device 30.

Specifically, the controller 37 assigns priorities to the conversation sentences based on information input through the input circuit 35, and selects at least one of the conversation sentences with a user. The controller 37 then provides various types of support based on either the input information or a result of the conversation with a user, etc.

The controller 37 has a function of identifying a patient. For example, the controller 37 identifies a patient so as to assign priorities to the conversation sentences suitable for the patient. The controller 37 controls the memory 38 to store information (personal information, biological information, and conversation information, etc.), which is categorized by patient. The controller 37 may access an external database for example, to download or upload information relating to a patient.

The controller 37 may have a function of learning the past conversations with each of the patients and support provided in the past for each of the patients, and may assign priorities to each of the conversation sentences and infer support to be provided based on learning results. The controller 37 may further possess a learning function to recognize a patient's voice and special terms pertaining to hospitals. For example, a recognition rate of language recognition software, which tends to be low if a user is of advanced age, may be improved with the use of such a learning function.

If the terminal device 30 is installed in a nursing robot, for example, the controller 37 may control to operate the robot in accordance with the conversations and the support, or may provide an operation instruction to a control system of the robot.

Some parts of the processing performed by the controller 37 may be performed by the host server 10.

The terminal device 30 may further have a display. For example, the terminal device 30 may input and output information by displaying the conversations on the display for a patient who has difficulties in having a conversation.

The terminal device 30 may display patient information upon a request of a nurse who is visiting a patient for a medical inquiry.

Furthermore, the terminal device 30 may have an alert switch for a nurse call.

The terminal device 30 may further have a video receive circuit and a camera. For example, if one terminal device 30 is assigned for a plurality of patients, the patients may be identified by face recognition based on image information obtained by the camera.

1.3 Example of Flow of Support Operation

Next, an example of an operation flow of providing support to a user by the support system 1 will be described with reference to FIGS. 3 and 4.

Figure 3:
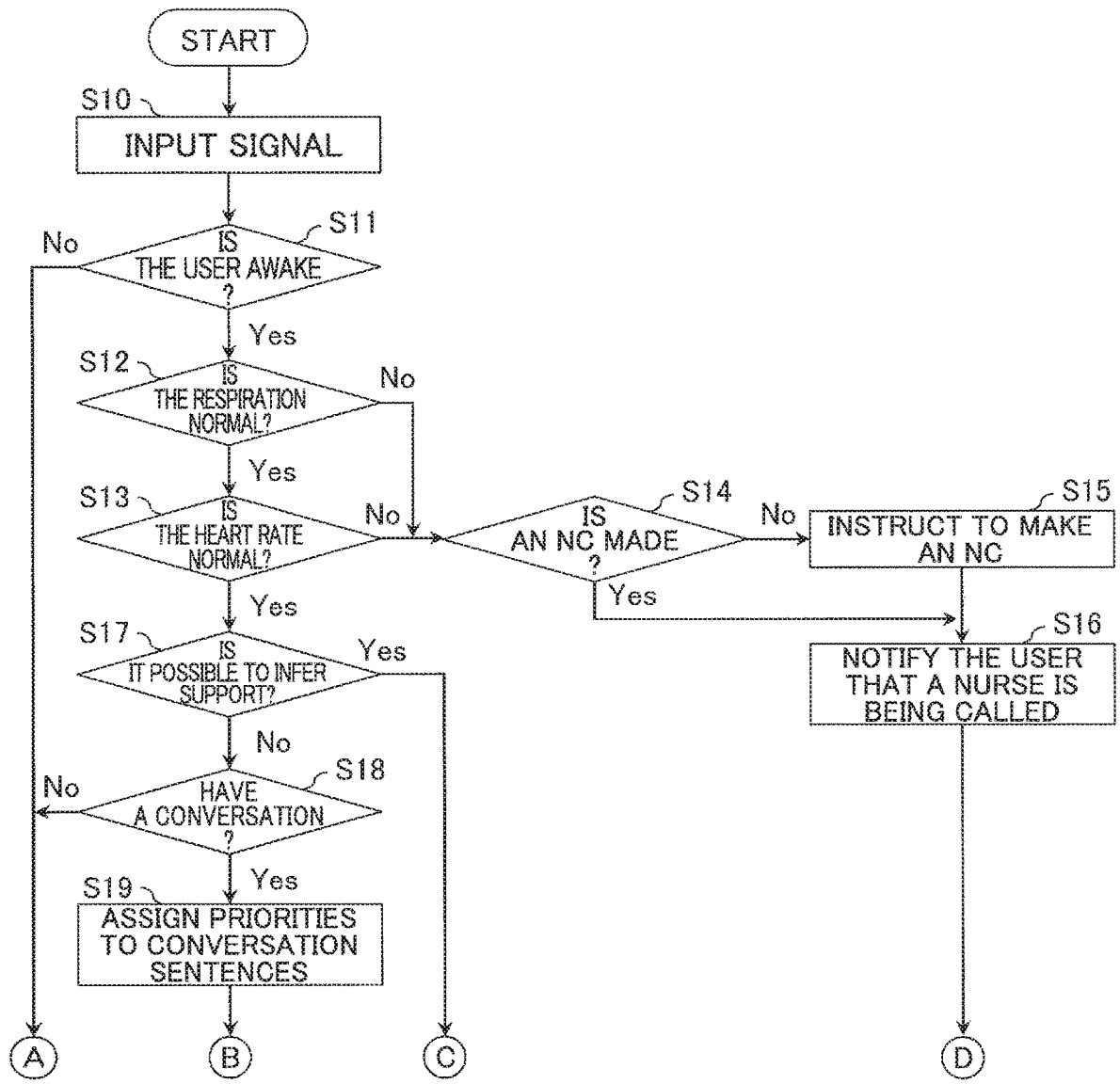
FIG. 3 is a flowchart a support operation in the support system of the first embodiment.

As shown in FIG. 3, if terminal device 30 receives an input of a signal (step S10), the controller 37 firstly starts a support operation. More specifically, the controller 37 starts a support operation in the following cases: if a signal notifying that a patient has made a nurse call (hereinafter "NC signal") is received from a nurse call management system; if the wakening signal, and a rise signal are received from Nemuri SCAN; if the controller 37 detects a respiration signal or a heart rate signal that has been being received from Nemuri SCAN exceed to a threshold value; or if a signal from the conversation switch 32 is received.

If terminal device 30 receives a waking signal, in other words, if a patient is awake (step S11_Yes), the controller 37 checks out whether the patient's respiration is within a normal range based on a respiration signal. On the other hand, if terminal device 30 doesn't receive a waking signal, that is, a patient is not awake (step S11_No), in other words, a patient is asleep, the controller 37 finishes the support operation.

If the patient's respiration is within a normal range (step S12_Yes), the controller 37 checks whether or not the patient's heart rate is within a normal range based on the heart rate signal. Note that the normal range for determining whether the patient's respiration is a normal is different from the normal range for determining whether the patient's heart rate is a normal.

If the patient's respiration exceeds the normal range, that is, abnormal (step S12_No), or if the patient's heart rate exceeds the normal range, that is, abnormal (step S13_No) the controller 37 checks whether or not an NC signal has been received, to then check whether or not a nurse call has been made.

If no nurse call has been made (step S14_No), the controller 37 transmits a signal instructing the management system to make a nurse call (step S15).

If a nurse call has been made (step S14_Yes), or after the management system is instructed to make a nurse call (step S15), the controller 37 notifies to a patient that a nurse (responder) is being called (step S16), and finishes the support operation. At this time, the controller 37 notifies to the nurse or the management system that the patient's respiration or heart rate exceeds the normal range. In other words, the controller 37 notifies that the emergency level of the nurse call is relatively high. In the example shown in FIG. 3, the controller 37 checks outpatient's respiration and heart rate if the patient is awake; however, if there are any abnormalities detected in the patient's respiration or heart rate, etc., regardless of whether the patient is awake or not, the controller 37 may prompt the patient to be awake, for example, and instruct the patient to make a nurse call.

If the patient's heart rate is within a normal range (step S13_Yes), the controller 37 infers support necessary for the patient (step S17_Yes). More specifically, the controller 37 infers types of necessary support (for example, support for appropriately responding to a sudden change in the patient's condition, providing assistance with excretion, supplying a bottle of water, controlling the peripheral equipment, or being a conversation partner, etc.) based on the following: frequencies and timing of a nurse's visit to a patient's room; treatment given by a nurse (e.g., responding to a sudden change in the patient's condition, providing assistance with excretion, preparing a wheelchair, supplying drinking water, etc.); a status of a peripheral equipment (e.g., lighting, curtains, or TV), statuses of other patients (e.g., if the other patients in the same room are asleep or awake); or values of various sensors (waking signal, rise signal respiration signal, or heart rate signal, etc.).

If it is difficult to infer necessary support (step S17_No), the controller 37 determines if the terminal device 30 determines to communicate with the patient.

If the terminal device 30 determines that there is no need to communicate with the patient (step S18_No), the controller 37 finishes the support operation. For example, the patient may fall asleep after being awake during the night. In such a case, the controller 37 may be configured to avoid unnecessary conversation with the patient, judging from a time of day.

If the terminal device 30 determines to communicate with the patient (step S18_Yes), the controller 37 assigns priorities to a plurality of conversation sentences stored in the memory 38 based on the input information, etc. (step S19), and determines at least one of the conversation sentences with the patient. More specifically, a conversation sentence that should be assigned higher priority is determined based on a time when the patient is awake, content of past conversations and support provided in the past, and patient's statuses (waking signals, rise signals, respiration signals, heart rate signals, etc.). For example, if, judging from the history of past conversations, the patient is likely to request a bottle of water after waking, the controller 37 assigned a high priority to a conversation sentence which asks the patient if he wants some water to drink. For example, if the patient sits up and moves to the edge of the bed, or if there is a high possibility that the patient desires to excrete, judging from a time of day or a result of an excretion sensor, etc., the controller 37 assigned a high priority to a conversation sentence for asking the patient if he requires the assistance of a nurse, or the provision of a wheelchair or an IV pole.

The controller 37 may determine a conversation sentence or volume of the conversation based on a time of day and statuses of other patients in the same room. More specifically, if the other patients are asleep using the terminal device 30, via access to other terminal devices 30, the controller 37 may select a conversation sentence for asking the patient to move out of the room, or may lower the volume of the conversation.

Figure 4:
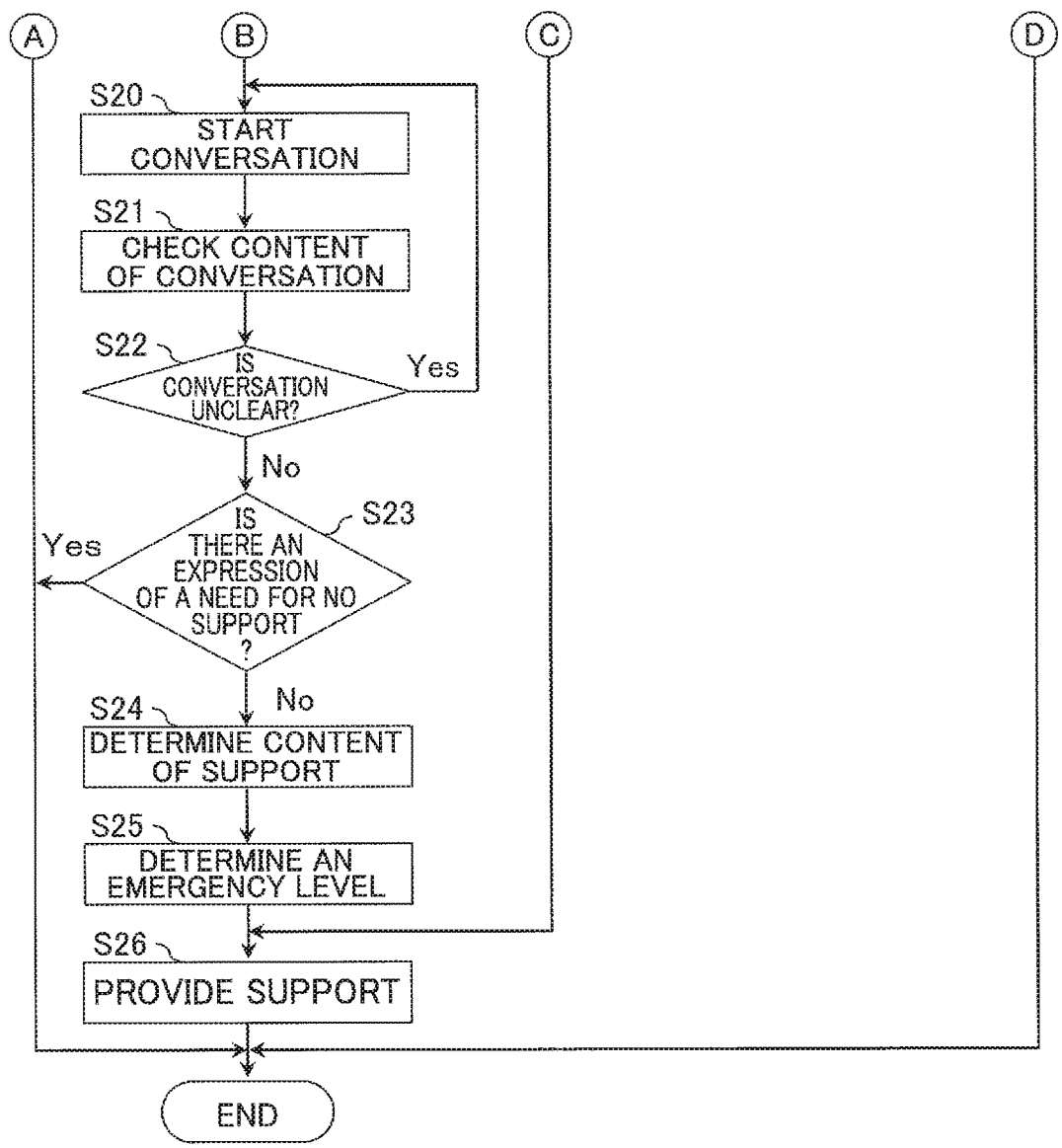
FIG. 4 is a flowchart of the support operation in the support system of the first embodiment.

As shown in FIG. 4, the terminal device 30 has a conversation with the patient based on the prioritized conversation sentences (step S20).

The controller 37 checks the content of the conversation which the patient speaks (step S21).

If the content of the conversation is unclear (step S22_Yes), in other words, the terminal device 30 doesn't follow what the patient has said, the process returns to step S20, and the terminal device 30 has a conversation with the patient once again, causing the circuit 37 to check the content of the conversation once again.

If the content of the conversation is clear (step S22_No), in other words, the terminal device 30 was able to understand the content of the conversation, the controller 37 determines whether or not support should be provided to the patient based on the content of the conversation.

If there is an expression indicating that the patient requires no support in the content of the conversation (step S23_Yes), the controller 37 finishes the support operation.

If the patient does not express the requirement of "no support" (step S23_No), in other words, if the patient needs support, the controller 37 determines the content of support (step S24), and then determines an emergency level of the support (step S25). For example, if the patient feels sick, the emergency level is relatively high; on the other hand, if the patient merely needs someone to talk to, the emergency level is relatively low.

The controller 37 provides support in accordance with the content of support and an emergency level of support (step S26). More specifically, if a nurse's support is necessary, for example, the controller 37 reports the content of support and an emergency level to a nurse.

For example, if there are nurse calls from more than one patient, a nurse can decide which patient's call should be prioritized based on a report result from the support system 1. For example, if the support system 1 is able to communicate with a system that arranges a nurse's visiting course and schedule, etc., the arranging system may carry out rearrangement of the visiting course and schedule based on information from the support system 1. In other words, a flow line of a nurse's operation can be reassessed based on information from the support system 1.

If a nurse's support is unnecessary, the support system 1 notifies a nurse not to need any support, and provides necessary support without the nurse. For example, if an automatic carrier, such as a wheelchair, a cart, or an IV pole, is necessary, the support system 1 transmits control signals to an automatic carrier device, and operates the device. For example, if the patient requests a bottle of water, the support system 1 transmits a control signal to an automatic carrier device for carrying a bottle of water so as to have the device bring a bottle of water to the patient. For example, if an operation of lighting, curtains, or TV, is necessary, the support system 1 transmits a control signal to such peripheral equipment. For example, if the patient needs someone to talk to, the terminal device 30 plays a role as a conversation partner.

For example, if the user is a nurse and requires patient's information for medical inquiry, the support system 1 reports patient's information stored in the memory 38 by voice, or provides the information to a medical information terminal device, etc. that the nurse carries, through a wireless communication, etc.

When the support is finished, the support system 1 finishes the support operation.

1.4 Advantageous Effects of the Embodiment

According to the configuration of the present embodiment, the support system 1 includes a terminal device 30, and provides support to patients through checking out a patient's (user's) condition, content of request, and an emergency level of request with the use of the terminal device 30. It is thereby possible to reduce responsibilities of nurses (care providers) who take care of patients, and improve efficiency of a nurse's operations. Advantageous effects will be described in detail below.

At a hospital, for example, upon a nurse call made by a patient, a nurse goes to the patient's room to deal with his request. However, if many nurse calls are made during period of time, such as night time, when fewer nurses are on duty, the possibility that a patient cannot be taken care of immediately increases due to a shortage of nurses.

Furthermore, patient requests vary from a sudden change of condition, when an emergency level is relatively high, to a need of a bottle of water, when the emergency level is relatively low. Since nurses often address patient's requests that need not necessarily be dealt with by nurses, burdens on nurses tend to be greater than necessary.

There are cases where a nurse first goes to a patient to check out his condition or ascertain his request, and then goes back to obtain what the patient requests (for example, a bottle of water, a wheelchair, a cart, or an IV pole, etc.). For this reason, it takes time to take care of a single patient, and the nurse's work efficiency tends to decrease.

Furthermore, if there are multiple nurse calls from more than one patient at the same time, the nurse cannot prioritize tasks without knowing the conditions or requests of each patient.

In contrast, with the configuration according to the present embodiment, the support system 1 can, upon the input of an NC signal relating to a nurse call, or biological information of a patient, check the content of necessary support based on the input information content and through conversations with a patient, and can provide support to the patient. For example, the support system 1 can transmit information, such as condition of a patient and an emergency level, to a nurse, in response to a request having a high emergency level, such as a sudden change in a patient's condition. It is thus possible for a nurse to prepare the items necessary for treatment in advance of going to a patient's room, and to perform treatment with a high degree of efficiency. A nurse can assign priorities to their jobs based on information provided by the support system 1.

For example, the support system 1 may perform some part of the support, in place of a nurse, such as carrying a bottle of water or operating peripheral equipment. It is thus possible to reduce the number of times a nurse has to give treatment to an individual patient, and consequently the burdens on a nurse.

Furthermore, with the configuration according to the present embodiment, the support system 1 can assign priorities to a plurality of conversation sentences based on the content of past conversation or support, and input information, etc., and can continue a conversation with the patient based on a result of the prioritization. It is thereby possible for a patient to convey their request to the support system 1 more quickly. Furthermore, the stress caused by having unnecessary conversation can be reduced.

In the present embodiment, a case where the support system 1 is used in a hospital is described; however, the above description applies to a case where the support system 1 is used by a care receiver at nursing facilities or by a home-care patient. It is preferable that content of support and conversation sentences, etc. are registered in advance depending on how the support system 1 is used.

2. Second Embodiment

Next, the second embodiment will be described. In the second embodiment, five examples of a support operation performed by the support system 1 will be given. Hereinafter, the matters differing from the first embodiment will be mainly described.

2.1 First Example

A first example will be described. In the first example, a nurse uses the support system 1 when visiting a patient for a medical inquiry.

The terminal device 30 according to the first example has a function of identifying a nurse. More specifically, for example, the terminal device 30 may have an inquiry button that shifts the terminal device 30 to an inquiry mode in which the terminal device 30 provides the nurse with a patient's information when the nurse pressed the button and may have a function of shifting the terminal device 30 to an inquiry mode when the controller 37 identifies a nurse based on an input of voice data, etc. by the nurse, or when the controller 37 obtains image information by a camera installed in a patient's room.

Next, a flow of the support operation will be described.

After the terminal device 30 is shifted to the inquiry mode, the terminal device 30 provides a nurse with a patient's information (for example, sleeping times of the day before, respiration during the sleep, heart rate, frequency of excretion) upon a request of the nurse. The nurse obtains information that cannot be gathered from a conversation with the patient, through the patient's information provided by the terminal device 30.

For example, after the terminal device 30 is shifted to the inquiry mode, the terminal device 30 may start a conversation with the patient upon an instruction from the nurse. When the nurse visits the patient for a medical inquiry, the nurse checks out the patient's condition, etc. based on a conversation with the patient. At this time, the nurse may communicate with the patient via the terminal device 30 to make the patient feel relaxed and to make conversation progress smoothly.

2.2 Second Example

Next, a second example will be described. In the second example, the terminal device 30 prompts a sleeping patient to go to a restroom to excrete.

The terminal device 30 talks to a patient who is asleep and prompts him to go to the restroom, in accordance with an input signal from an excretion sensor attached to the patient, or a time.

2.3 Third Example

Next, a third example will be described. In the third example, a patient receives rehabilitation for a speech disorder by using the terminal device 30.

The terminal device 30 according to the third example has a function of image recognition, for example. More specifically, the terminal device 30 includes a camera, and has a function of recognizing cards used for rehabilitation for the speech disorder with the use of the camera. The terminal device 30 has a rehabilitation mode for providing assistance to a patient in rehabilitation.

Next, a flow of the support operation will be described.

The terminal device 30 starts a conversation with the patient when the conversation switch 32 is operated by the patient, and is shifted to the rehabilitation mode in response to the patient's request.

For example, in the rehabilitation mode, when the patient pronounces a name of something on a card, the terminal device 30 judges the pronounced name based on the comparison result of the pronounced name and the name of something on the card displayed on the camera. If the patient's answer is incorrect or pronunciation is unclear, the terminal device 30 supports the patient by voice and helps the patient to make the correct pronunciation. The terminal device 30 may summarize a result of rehabilitation. For example, the terminal device 30 may compare the result with a result of past rehabilitation so as to check out a recovery status of the patient.

2.4 Fourth Example

Next, a fourth example will be described. In the fourth example, the terminal device 30 analyzes a patient's emotions based on a conversation with a patient.

The terminal device 30 analyzes the patient's emotions from how the patient answers or replies in a conversation, a sound volume, and conversation speed, etc. As a result, the terminal device 30 may assign priorities to conversation sentences so as to make a patient's mental status stability.

2.5 Fifth Example

Next, a fifth example will be described. In the fifth example, the support system 1 is used for home nursing and home care.

For example, in the home nursing, the terminal device 30 receives patient's biological information from a monitoring device, such as Nemuri SCAN. If terminal device 30 detects the patient's biological information exceeds a normal range, or if terminal device 30 detects an abnormal patient's response in a conversation, the terminal device 30 may prompt the patient to contact a hospital, or directly contact a hospital. The terminal device 30 may talk to the patient at a determined point in time to prompt the patient to take medicines, sleep, undergo rehabilitation, or excrete.

2.6 Advantageous Effects of Second Embodiment

The configuration of the present embodiment achieves advantageous effects similar to those achieved by the first embodiment.

Furthermore, with the configuration according to the first example of the present embodiment, the support system 1 can provide nurses with more detailed information regarding patients than information obtained through conversations with patients. It is thereby possible for nurses to conduct physical condition management for patients more effectively.

Furthermore, with the configuration according to the second example of the present embodiment, the support system 1 can talk to a sleeping patient with an intention of waking him up, as needed. It is thereby possible to decrease the possibility that the patient fails at excretion.

Furthermore, with the configuration according to the third example of the present embodiment, the support system 1 can support a patient in rehabilitation. For example, the support system 1 can conduct a part of rehabilitation for speech disorder, which usually requires the assistance of a nurse or a physiotherapist, etc. It is thereby possible to reduce burdens on a nurse or a physiotherapist. Furthermore, a patient can receive rehabilitation more effectively when their physical or mental condition allows.

Furthermore, with the configuration according to the fourth example of the present example, the support system 1 analyzes the patient's emotions through a conversation with a patient. It is thereby possible for a nurse to know a patient's mental status.

Furthermore, with the configuration according to the fifth example of the present embodiment, the support system 1 can detect any abnormal status of a home-care patient (or home-care receiver), and talks to a home-care patient as needed.

3. Third Embodiment

The third embodiment will be described below. In the third embodiment, one terminal device 30 responds more than one patient in a patient's room. Hereinafter, the matters differing from the first embodiment will be mainly described.

3.1 Example of Flow of Support Operation

An example of an operation flow of providing support to a user by the support system 1 will be described with reference to FIG. 5.

Figure 5:
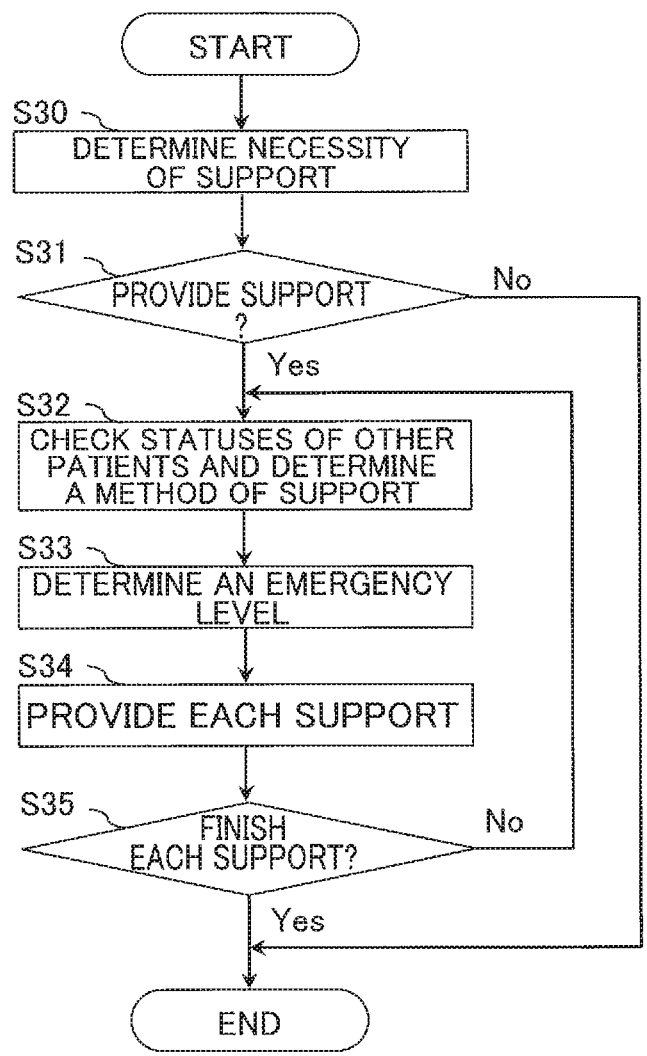
FIG. 5 is a flowchart of a support operation in the support system of a third embodiment.

As shown in FIG. 5, the controller 37 determines whether or not support should be provided to one patient (step S30). More specifically, the controller 37 determines necessity provide any support in accordance with the flow from step S10 through step S24 described in the first embodiment with reference to FIGS. 3 and 4.

If the controller 37 determines to provide support (step S31_Yes), the controller 37 checks out the statuses of the other patients, and determines the content of support and a support method in accordance with the statuses (step S32).

For example, the controller 37 determines a method of conversation with a patient based on whether or not the other patients are asleep. More specifically, if the other patients are asleep, for example, the controller 37 may communicate with the patient at a volume smaller than a normal setting. For example, if the terminal device 30 has a directive speaker, the controller 37 may use the directive speaker to have a conversation with the patient. For example, if the terminal device 30 is installed on a robot, the controller 37 may convey the content of a conversation to the patient through gestures (actions) of the robot. For example, if the terminal device 30 has a display, the controller 37 may display the content of a conversation on the display, instead of talking to the patient.

For example, the controller 37 knows the whereabouts of the other patients, and determines a support method in accordance with those whereabouts. More specifically, if another patient blocks the way when a patient goes to the restroom, for example, the controller 37 may talk to the another patient to give way to the patient who goes to the restroom. For example, if a patient is looking for any other patient, the controller 37 may inform the other patient by saying "[Someone] is looking for you".

For example, it controller 37 receives requests from more than one patient, the controller 37 ascertains the requests and determines a support method in accordance with the content of respective requests. More specifically, if the nurse can respond to the requests from more than one patient in the same patient's room in a single visit, the controller 37 may notify this to the nurse. For example, suppose a case where the changing of a diaper and the supply of a bottle of water are requested; if the nurse makes preparations to meet both of the requests in advance of a visit to the patient's room, the nurse can carry out this support on this single visit.

After the controller 37 determined the support method in step S32, the controller 37 determines an emergency level of content of support to be provided to each patient (step S33).

The controller 37 provides support to respective patients in a descending order of emergency level (step S34). In this case, the controller 37 provides support simultaneously in response to requests that can be processed in parallel.

More specifically, if more than one patient need a nurse call, the controller 37 may inform a nurse in this regard by making one nurse call. For example, if more than one patient requests for a bottle of water, a wheelchair, a cart, or an IV pole, etc., to be carried to them, the controller 37 may contact the automatic carrier device about these requests, and make arrangements for the requests in a batch. For example, if more than one patient requests for someone to talk to, the controller 37 may communicate with them. For example, during a medical inquiry by a nurse, the controller 37 may report information pertaining to respective patients in a batch to the nurse. For example, if more than one patient requests for an operation of peripheral equipment, the controller 37 may perform the operations of lighting, curtains, or TV simultaneously.

The controller 37 confirms the completion of each support. If each support operation is not finished (step S35_No), the controller 37 returns to step S32.

More specifically, if controller 37 receives an additional request, the controller 37 firstly checks out whether the support in the past has already been finished, and then returns to step S32 to determine content of support and a method of support. For example, if a nurse has already been called to provide other support, the controller 37 may inform the nurse about the additional request, without making another nurse call.

If each support operation is finished (step S35_Yes) the controller 37 finishes the support operation.

In the present embodiment, one terminal device 30 is installed in one patient's room; however, one terminal device 30 may be given to each patient. In this case, the host server 10 may perform processes, such as determining a support method after checking statuses of other patients and determining an emergency level of each request.

3.2 Advantageous Effects of Third Embodiment

The configuration of the present embodiment achieves advantageous effects similar to those achieved by the first and second embodiments.

Further, according to the configuration of the present embodiment, the support system 1 can determine content of support, a support method, and an emergency level, in accordance with statuses of other patients. Furthermore, the support system 1 can respond to multiple requests in a batch. It is thereby possible for a nurse to respond to requests in a descending order of emergency level. Furthermore, a nurse can respond multiple requests at once. It is thereby possible to improve the efficiency of a nurse's operations.

4. Fourth Embodiment

The fourth embodiment will be described below. In the fourth embodiment, an example of a status of a patient and his peripheral circumstances for the support system 1 to determine whether or not to talk to (provide support to) the patient, will be described. Hereinafter, the matters differing from the first to third embodiments will be mainly described.

4.1 Examples of Patient's Statuses and Circumstances in which the Decision to Talk to Patient is Determined First, a status of a patient, and his circumstances when the terminal device 30 of the support system 1 determines whether or not to talk to the patient, is described. If a trigger that necessitates talking to a patient is activated in the terminal device 30, there are seven statuses of a patient, or his circumstances, for determining whether the terminal device 30 should talk to the patient or not, as follows:

First Status: A patient being asleep

Second Status: A patient being awake

Third Status: whether the patient follows the instruction of nurse (For example, the instruction is set by medical professionals)

Fourth Status: Ambient sound being relatively loud, or ambient light being relatively bright around the terminal device 30

Fifth Status: Ambient sound being relatively small, or ambient light being relatively dark around the terminal device 30

Sixth Status: Treatment history of a patient

Seventh Status: Change in patient's vital condition

More specifically, for the first and second statuses, the terminal device 30 (controller 37) ascertains if a patient is asleep or awake based on information obtained from Nemuri SCAN, for example. If, the patient is asleep, the controller 37, for example, determines talking to the patient to be unnecessary and does not talk to the patient (does not have a conversation with the patient). If the patient is awake, the controller 37, for example, determines a conversation with the patient to be possible, and talks to the patient. The controller 37 may ascertain a patient's life rhythm based on the first to seventh statuses in advance, and determine the necessity of talking to a patient. More specifically, for example, the controller 37 determines that talking to the patient is unnecessary based on the ascertained life rhythm, even if the patient is awake during his usual sleeping hours, and does not talk to the patient.

Regarding to the third status, examples of the instruction of nurse (instruction of responder) are instructed times of taking medicines, instructed times to take rehabilitation, and restrictions the patient sleeps in the daytime. If the instruction of nurse is the "instructed times of taking medicines" or "instructed times to take rehabilitation", the controller 37 talks to a patient so as to take medicines or to take rehabilitation if a set time passed. If the instruction of nurse is the "restrictions the patient sleeps in the daytime", the controller 37 talks a patient so as to wake up if the patient seems to fall asleep during the restricted time.

For the third status, the controller 37 talks to a patient who needs to be managed at every time to check out his condition, for example. The controller 37, asks a patient about an amount of food and drinks after a meal time, for example.

For the fourth and fifth statuses, a sensor for sensing sound and light around the terminal device 30, for example, is included in the terminal device 30. The controller 37 ascertains a circadian rhythm of a patient from ambient sound and ambient light, for example. The terminal device 30 may further includes a detector which can detect how bright the ambient light is based on a threshold value, and the microphone 33 in the terminal device 30 can detect how large ambient sound is. The terminal device 30 determines the status of the patient as a status that the patient is awake if the ambient sound is relatively large, or the ambient light is relatively bright. The terminal device ascertains a circadian rhythm of a patient based on a history of everyday timing the patient wakes up.

The controller 37 talks to the patient, if ambient sound is relatively loud or ambient light is relatively bright, for example day time. The controller 37 does not talk to the patient if ambient sound is relatively quiet or ambient light is relatively dark, for example night time (or sleeping time). For example, the controller 37 may talk to the patient, even if the patient is asleep, to prompt the patient to wake up based on the circadian rhythm when a wake-up time comes. The wake-up time is set by the staff and the patient.

For the sixth status, the controller 37 ascertains the treatment history of a patient from information of a patient's electronic medical record or a body movement status, and talks to the patient as appropriate. For example, the controller 37 notifies the patient of the time at which to take medicines. For example, the controller 37 alerts the patient when anesthesia wears off. For another example, the controller 37 notifies the patient of a time to change his body position.

For the seventh status, the controller 37 ascertains vital information that can be obtained from Nemuri SCAN or a smart bed, etc. that can measure vital data of a user, and talks to the patient as appropriate. For example, the controller 37 talks to the patient when it detects abnormalities in the patient's vital data (whether the patient's vital data is outside the normal range) and checks out the patient's condition.

4.2 Examples of Determination of Whether or not to Talk to a Patient Based on a Combination of Two Statuses Next, specific examples of determination of whether or not to talk to a patient based on a combination of two statuses will be described using FIG. 6. The example shown in FIG. 6 is that the controller 37 determines whether or not to talk to a patient based on a combination of two statuses among the above-described first to seventh statuses. The controller 37 determines whether or not to talk to a patient in accordance with a combination of three or more statuses.

As shown in FIG. 6, if a combination of two statuses is used to determine whether or not to talk to the patient, the controller 37 determines each of the statuses, a first-priority status and a second-priority status.

A case where the third status is the first-priority status is described.

If the first status (being asleep) is a second-priority status, the controller 37 will basically talks to the patient if the controller 37 finds out the patient doesn't follow the nurse's instruction, even if the patient is sleeping. Furthermore the controller 37 may determine whether or not to talk to the patient based on an emergency level of content of a nurse's instruction (for example, time to take medicine, time to take rehabilitation, time to end a nap, etc.) If the emergency level of the instruction the patient doesn't follow is relatively low, the controller 37 doesn't talk to the patient. If the emergency level of the instruction the patient doesn't follow is relatively high, the controller 37 need to talk to the patient.

The emergency level of the nurse's instruction related to time to take medicines is relatively high that of the nurse's instruction related to restrictions the patient sleeps in the daytime, for example.

Then, if the controller 37 determines that talking to the patient is necessary, the controller 37 talks to the patient.

If the second status (being awake) is a second-priority status, the controller 37 talks to the patient in accordance with content of the instruction.

A case where the fourth status (ambient sound: relatively large (loud), ambient light: relatively bright) is a first-priority status is described.

If the first status (being asleep) is a second-priority status, the controller 37 talks to the patient judging that it is a time to wake up based on the ambient sound and ambient light, even if the patient is sleeping.

If the second status (being awake) or the third status (nurse's instruction) is a second-priority status, the controller 37 talks to the patient in accordance with the content of support.

A case where the fifth status (ambient sound: relatively small, ambient light: relatively dark) is a first-priority status is described.

If the first status (being asleep) is a second-priority status, the controller 37 does not talk to the patient.

If the second status (being awake) is a second-priority status, the controller 37 does not talk to the patient, even if the patient is awake when the controller 37 determines that it is time to sleep based on the ambient sound and ambient light.

If the third status (nurse's instruction) is a second-priority status, the controller 37 determines talking to the patient to be unnecessary for a nurse's instruction with a low emergency level, for example, if the controller 37 determines that it is time to sleep.

A case where the sixth status (history of treatment) is the first-priority status is described.

If the first status (being asleep) is a second-priority status, the controller 37 will basically talks to the patient if the controller 37 finds out the time the patient need to change body position passes, even if the patient is sleeping. The six status includes whether the time the patient need to take medicines passes, whether the time the patient need to take rehabilitation passes, whether the predetermined time passes after anesthesia wears off, or whether the time the patient need to change body position passes, for example. Furthermore the controller 37 may determine whether or not to talk to the patient based on the patient's history of treatment, for example, time to take medicine, time to take rehabilitation, time when anesthesia wears off, time to change body position, even when the patient is sleeping.

If the second status (being awake), the third status (nurse's instruction), or the fourth status (ambient sound: relatively large (loud), ambient light: relatively bright) is a second-priority status, the controller 37 talks to the patient in accordance with the content of support. If the fifth status (ambient sound: relatively small, ambient light: relatively dark) is a second-priority status, the controller 37 talks to the patient if an emergency level is determined to be high based on the history of treatment, even during sleeping hours.

A case where the seventh status (change in vital conditions) is a first-priority status is described.

If the controller 37 detects any abnormalities in the vital conditions (for example, if a vital condition exceeds a determination standard that is predetermined by a medical professional), the controller 37 talks to the patient, regardless of the status that has been designated as second priority.

4.3 Advantageous Effects of Fourth Embodiment

The configuration of the present embodiment achieves advantageous effects similar to those achieved by the first embodiment.

Furthermore, according to the configuration of the present embodiment, the support system 1 can determine the necessity of talking to a patient depending on a plurality of circumstances, and can provide more suitable support.

5. Fifth Embodiment

The fifth embodiment will be described below. In the fifth embodiment, two examples of using the support system 1 at, for example, a hotel will be described. In the following examples, the terminal device 30 of the support system 1 is installed in each room. Each hotel guest (user) may be provided with one terminal device 30 of the support system 1. In the following, only the matters differing from the first through fourth embodiments will be described.

5.1 First Example

First, the first example will be described with reference to FIG. 7. The example shown in FIG. 7 shows a case where the support system 1 estimates a time when a guest wakes up, and arranges preparation of breakfast for the guest.

Figure 7:
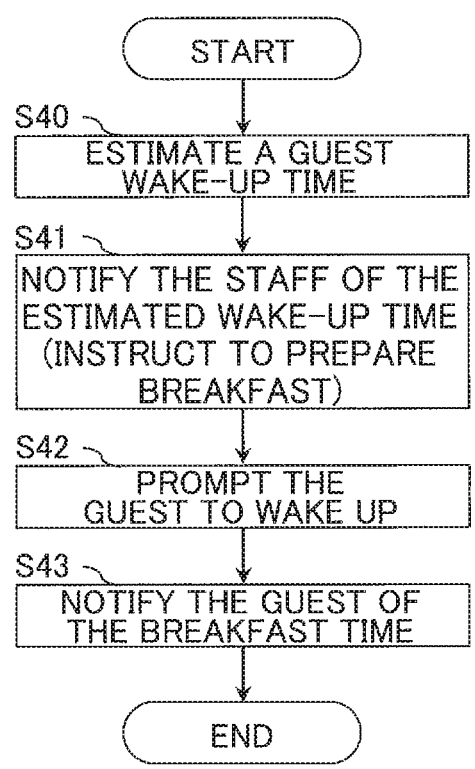
FIG. 7 is a flowchart of a support operation in the support system of a first example of a fifth embodiment.

As shown in FIG. 7, the terminal device 30 (controller 37) ascertains a sleeping rhythm of a guest based on information of a waking signal that can be obtained from Nemuri SCAN installed in the bed, or information from a camera, for example. The controller 37 ascertains a circadian rhythm from ambient sound and ambient light around the terminal device 30. The controller 37 estimates a time when the guest can comfortably wake up based on the information (step S40).

Next, the host server 10 of the support system 1 notifies hotel staff (responder) of the estimated wake-up time obtained by the terminal device 30, and instructs the hotel staff to prepare breakfast (step S41). More specifically, for example, the controller 37 determines a time for breakfast based on the estimated wake-up time and a predetermined preparation time between when the guest wakes up and when the guest starts having breakfast. The host server 10 then notifies the hotel staff of the estimated wake-up time and breakfast time obtained from the terminal device 30. At this time, for example, the host server 10 may notify a restaurant of a busy breakfast hour estimated from the breakfast time of each guest.

Next, the controller 37 starts providing support at the estimated wake-up time. For example, the controller 37 prompts the guest to wake up comfortably through talking to the guest (step S42).

Subsequently, the controller 37 notifies the woken-up guest of the breakfast time (step S43). The support system 1 also notifies the staff that the guest is awake.

5.2 Second Example

Now, the second example will be described with reference to FIG. 8. In the second example, a case where the support system 1 determines an emergency level of a support request from each room (terminal device 30) and notifies the hotel staff of the emergency level, will be described. The support request includes a request for room services, a request for massage, or a request for changing linen used in a room, for example.

Figure 8:
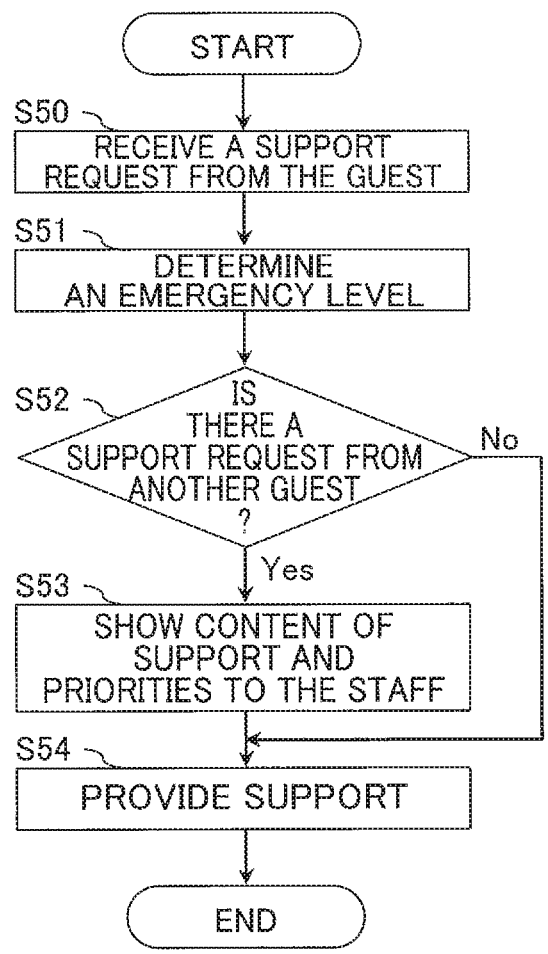
FIG. 8 is a flowchart of a support operation in the support system of a second example of the fifth embodiment.

As shown in FIG. 8, the controller 37 receives a support request from a guest (step S50). The controller 37 that has received the support request determines an emergency level of the support request in accordance with the content of the request, camera information, tone of the guest's voice, etc. (step S51), and notifies the host server 10 of information regarding the content of support and the emergency level.

Since the patient can't sleep well, the controller 37 treats a received request as high emergency level if the controller 37 received request of changing linen used for the bed in a room in the middle of night. The controller 37 treats a received request as high emergency level if the tone of the guest voice seems to be strange or pretty loud.

Next, upon the receipt of the information regarding the content of support and the emergency level from the terminal device 30, the host server 10 checks out whether there is any other support request from other guest, namely another terminal device 30 (step S52).

If there are no support requests from other guest (step S52_No), the host server 10 notifies the staff that there is a support request. The staff provides support based on the support request received from the host server 10 (step S54).

If there is a support request from another guest (step S52_Yes), the host server 10 displays the content of each support and the priorities to the staff, based on the emergency level of each support (step S53).

Next, the staff provides support based on the priorities displayed by the host server 10 (step S54).

5.3 Advantageous Effects of Fifth Embodiment

According to the configuration of the present embodiment, the support system 1 can ascertain a status of a guest (user) through the terminal device 30 (for example, whether a guest is asleep, awake, hurry, or angry), and thus determine when to provide support. Thus, the staffs can handle requests without offending guests.

Furthermore, according to the configuration of the present embodiment, the support system 1 assigns priorities to support requests made by more than one guest, and displays the priorities to the staff. It is thereby possible to improve the efficiency of staff work, and to reduce the stress levels of guests waiting for support.

6. Sixth Embodiment

Next, the sixth embodiment will be described. In the sixth embodiment, two examples where the support system 1 is installed in a user's house will be described. In the following, only the matters different from the first through fifth embodiments will be described.

6.1 First Example

First, a first example will be described. In the first example, a support operation based on a life rhythm of a user will be described.

For example, in a user's house, the controller 37 ascertains a use s daily life rhythm (e.g., bedtime) from information obtained from Nemuri SCAN or information obtained from a camera, etc. The controller 37 then determines a recommendation bath time that assures the user of a good sleep based on his bedtime. The controller 37 then prompts the user to take a bath when the recommended bath time comes.

6.2 Second Example

Next, a second example will be described. In the second example, an example of a support operation performed for a case where a user is an elderly person living alone, will be described.

For example, the support system 1 ascertains the user's living circumstance from the user's actions in the house, or responses to conversations and the like, and reports the statuses of a user's physical ability and cognitive ability to a family member (responder) who lives in a different place. Based on the report from the support system 1, the family member may consult a doctor or adjust the number of visits, for example.

6.3 Advantageous Effects of Sixth Embodiment

According to the configuration of the present embodiment, the support system 1 can ascertain a us life rhythm and provide support based on the life rhythm. The support system 1 ascertains a user's life rhythm and can report a life circumstance to the responder. It is thereby possible for the responder to provide support appropriate.

7. Modification, Etc.

The embodiments are not limited to the above-described aspects, but can be modified in various ways.

For example, the controller 37 may visualize an emergency level of a patient's request with the use of an index, and notify a nurse of the patient's request.

Furthermore, the controller 37 may determine body condition when the patient wakes up based on a signal that can be obtained from Nemuri SCAN, for example, and report the determination result to the nurse.

Furthermore, the controller 37 may have a learning function for learning information, such as frequencies of wake-ups or vital conditions (respiration, heart rate, and so on). The controller 37 may determine the presence/absence of a conversation with the patient based on a result of this learning function.

Furthermore, the controller 37 may learn a relationship between the content of conversations and differences in smoothness in response, and may automatically change the priorities of the conversation sentences.

The present invention is not limited to the above embodiments, but can be modified in various forms, without departing from the gist thereof. The respective embodiments may be appropriately combined and practiced. In this case, a combined effect is obtained. The above-described embodiment incorporates various kinds of inventions which can be extracted by combinations selected from the plurality of disclosed constituent elements. For example, even if some constituent elements are deleted from all the constituent elements disclosed in the embodiment, an arrangement from which some constituent elements are deleted can be extracted as an invention as long as the problem can be solved and the effect obtained.

What is claimed is:

1. A support system comprising: a server; and a terminal device capable of communicating with the server, wherein the terminal device includes, an input circuit configured to receive a first signal of a user, the first signal indicating whether the user is awake using biological information of the user; and a controller coupled to the input circuit and configured to determine whether an abnormal condition of the user exists based on the biological information of the user, the controller being configured to activate an alarm if the controller determines the abnormal condition of the user exists and is awake based on the first signal and the biological information of the user, and the controller being configured to provide support to the user if the controller determines the abnormal condition of the user does not exist and is awake based on the first signal and the biological information of the user, the support being different from the alarm, wherein the controller is configured to determine to talk to the user based on a first priority status and a second priority status, when the first priority status indicates an instruction of a responder and the second priority status indicates that the user is asleep, the controller is configured to determine to talk to the user in accordance with an emergency level of the instruction of the responder, and when the first priority status indicates the instruction of the responder and the second priority status indicates that the user is awake, the controller is configured to talk to the user in accordance with the instruction, wherein the controller is configured to check a content of a conversation with the user.

2. The system according to claim 1, wherein the input circuit is configured to receive a second signal relating to a call request by the user, and the controller is configured to check out a physical condition of the user based on the biological information of the user when receiving the second signal.

3. The system according to claim 1, wherein the terminal device further includes a switch for the user to start a conversation with the terminal device or to finish the conversation with the terminal device.

4. The system according to claim 1, wherein the controller is configured to execute a function of identifying the user, and is configured to assign priorities to conversation sentences suitable for the identified user.

5. The system according to claim 1, wherein the controller is configured to provide information of the user to the responder in response to a request from the responder.

6. The system according to claim 1, wherein the input circuit is configured to receive an input signal from an excretion sensor, and the controller is configured to prompt the user to excrete based on the input signal.

7. The system according to claim 1, wherein the controller has a rehabilitation mode that provides assistance to the user in rehabilitation.

8. The system according to claim 1, wherein the controller is configured to determine to talk to the user based on a third priority status and a fourth priority status, and when the third priority status indicates a sound and a light around the terminal device and the fourth priority status indicates that the user is asleep, the controller is configured to ascertain a circadian rhythm of the user from the sound and the light and determine to talk to the user at a wake-up time.

9. The system according to claim 1, wherein a content of the support includes a report of a state of at least one of a physical ability and a cognitive ability of the user to the responder.

10. The system according to claim 1, wherein the input circuit is configured to receive at least one of a respiration signal and a heart rate signal of the user.

11. The system according to claim 10, wherein the controller is configured to prompt the user to wake up based on at least one of the respiration signal and the heart rate signal.

12. The system according to claim 1, wherein the controller is configured to estimate a time when the user wakes up based on the first signal, and the server is configured to notify the responder of the estimated time.

13. The system according to claim 12, wherein the controller is configured to determine a time to start providing support based on the time when the user wakes up.

14. The system according to claim 1, wherein the controller is configured to provide the support to the user after the controller determines a content of the support and an emergency level of the support based on a result of the conversation with the user.

15. The system according to claim 14, wherein the content of the support includes content of a request by the user and the emergency level of the support.

16. The system according to claim 14, wherein the content of the support includes a transmission of a control signal to an external device.

17. The system according to claim 14, further comprising: a plurality of terminal devices, the terminal device being one of the plurality of terminal devices, wherein when the server receives a plurality of support requests from the plurality of terminal devices, the server is configured to notify the responder of content of each support and priorities based on an emergency level of each support.

18. A support system comprising:
a server; and
a terminal device capable of communicating with the server,
wherein the terminal device includes,
an input circuit configured to receive a first signal of a user, the first signal indicating that the user is awake; and
a controller coupled to the input circuit and configured to determine to provide support to the user based on the first signal, wherein
the controller is configured to analyze emotions of the user based on a conversation with the user.

19. A support system comprising:
a server; and
a terminal device capable of communicating with the server,
wherein the terminal device includes,
an input circuit configured to receive a first signal of a user, the first signal indicating that the user is awake; and
a controller coupled to the input circuit and configured to determine to provide support to the user based on the first signal, wherein
the controller is configured to determine to talk to the user based on a first priority status and a second priority status, and
when the first priority status indicates a history of treatment and the second priority status indicates that the user is asleep, the controller is configured to determine to talk to the user in accordance with the history of treatment.

* * * * *